United States Patent
Chong et al.

(10) Patent No.: US 9,107,673 B2
(45) Date of Patent: Aug. 18, 2015

(54) IRRIGATION CATHETER

(75) Inventors: Evan Chong, South Strathfield (AU); Zoran Milijasevic, Bayview (AU); Neil L. Anderson, Roseville (AU)

(73) Assignee: CATHRX LTD., Homebush Bay, New South Wales (AU)

( * ) Notice: Subject to any disclaimer, the term of this patent is extended or adjusted under 35 U.S.C. 154(b) by 1144 days.

(21) Appl. No.: 12/158,658

(22) PCT Filed: Nov. 27, 2006

(86) PCT No.: PCT/AU2006/001791
§ 371 (c)(1),
(2), (4) Date: Dec. 22, 2008

(87) PCT Pub. No.: WO2007/070920
PCT Pub. Date: Jun. 28, 2007

(65) Prior Publication Data
US 2009/0281538 A1    Nov. 12, 2009

Related U.S. Application Data

(60) Provisional application No. 60/753,836, filed on Dec. 23, 2005.

(51) Int. Cl.
*A61M 31/00* (2006.01)
*A61B 18/14* (2006.01)
(Continued)

(52) U.S. Cl.
CPC ............. *A61B 18/1492* (2013.01); *A61B 18/14* (2013.01); *A61B 2017/003* (2013.01); *A61B 2018/00178* (2013.01); *A61B 2018/1472* (2013.01); *A61B 2019/464* (2013.01)

(58) Field of Classification Search
USPC ............ 600/374, 381, 534, 564, 585; 604/20, 604/95.01, 95.04; 606/15, 27, 33, 34, 41, 606/49; 128/784
See application file for complete search history.

(56) References Cited

U.S. PATENT DOCUMENTS 4,301,802 A * 11/1981 Poler ............................... 606/48
4,370,982 A * 2/1983 Reilly ........................ 604/97.03
(Continued)

FOREIGN PATENT DOCUMENTS

EP    1 498 080 A1    1/2005
JP    11-262530       9/1999
(Continued)

OTHER PUBLICATIONS

International Search Report mailed on Feb. 7, 2007, for PCT Application No. PCT/AU2006/001791, filed on Nov. 27, 2006, one page.
(Continued)

*Primary Examiner* — Scott Medway
(74) *Attorney, Agent, or Firm* — TraskBritt

(57) ABSTRACT

An irrigation catheter assembly comprises an electrode sheath mount for mounting an electrode sheath. The mount has a laterally arranged aperture defined in it through which conductors for electrodes of the electrode sheath pass, in use. A connector, to which a source of irrigation fluid is connectable, is connected to a proximal end of the electrode sheath mount. The connector communicates with an interior of the mount so that, in use, fluid passes through the lumen of the electrode sheath to be delivered to a distal end of the electrode sheath.

24 Claims, 4 Drawing Sheets

(51) Int. Cl.
*A61B 17/00* (2006.01)
*A61B 18/00* (2006.01)
*A61B 19/00* (2006.01)

(56) References Cited

U.S. PATENT DOCUMENTS

| | | | |
|---|---|---|---|
| 4,644,960 A * | 2/1987 | Johans | 607/122 |
| 4,896,671 A * | 1/1990 | Cunningham et al. | 600/374 |
| 4,940,064 A * | 7/1990 | Desai | 607/122 |
| 5,125,895 A * | 6/1992 | Buchbinder et al. | 604/95.01 |
| 5,281,212 A * | 1/1994 | Savage et al. | 606/15 |
| 5,348,554 A * | 9/1994 | Imran et al. | 606/41 |
| 5,349,942 A * | 9/1994 | Heimberger | 600/139 |
| 5,431,168 A * | 7/1995 | Webster, Jr. | 600/435 |
| 5,462,544 A * | 10/1995 | Saksena et al. | 606/15 |
| 5,500,012 A * | 3/1996 | Brucker et al. | 607/122 |
| 5,643,197 A * | 7/1997 | Brucker et al. | 604/20 |
| 5,807,395 A * | 9/1998 | Mulier et al. | 606/41 |
| 5,922,004 A | 7/1999 | DuBois | |
| 5,964,757 A * | 10/1999 | Ponzi | 606/45 |
| 6,006,137 A * | 12/1999 | Williams | 607/119 |
| 6,198,974 B1 * | 3/2001 | Webster, Jr. | 607/122 |
| 6,409,724 B1 * | 6/2002 | Penny et al. | 606/41 |
| 6,551,283 B1 * | 4/2003 | Guo et al. | 604/167.06 |
| 6,602,242 B1 * | 8/2003 | Fung et al. | 604/528 |
| 6,699,243 B2 * | 3/2004 | West et al. | 606/41 |
| 7,104,989 B2 * | 9/2006 | Skarda | 606/41 |
| 7,285,116 B2 * | 10/2007 | de la Rama et al. | 606/27 |
| 7,824,406 B2 * | 11/2010 | Wang et al. | 606/45 |
| 7,857,810 B2 * | 12/2010 | Wang et al. | 606/41 |
| 7,914,528 B2 * | 3/2011 | Wang et al. | 606/41 |
| 2002/0198520 A1 * | 12/2002 | Coen et al. | 606/41 |
| 2004/0092806 A1 | 5/2004 | Sagon et al. | |
| 2006/0270969 A1 * | 11/2006 | Toyonaga et al. | 604/21 |

FOREIGN PATENT DOCUMENTS

| | | |
|---|---|---|
| JP | 2005-144175 | 6/2005 |
| WO | 96/10961 | 4/1996 |
| WO | WO0232497 | 4/2002 |
| WO | 2006012668 | 2/2006 |

OTHER PUBLICATIONS

U.S. Appl. No. 60/753,836, filed Dec. 23, 2005, by Chong et al.
Written Opinion mailed on Feb. 7, 2007, for PCT Application No. PCT/AU2006/001791, filed on Nov. 27, 2006, three pages.
Supplementary European Search Report dated Jan. 1, 2012 for EP Application No. 06804562.4-1285.

* cited by examiner

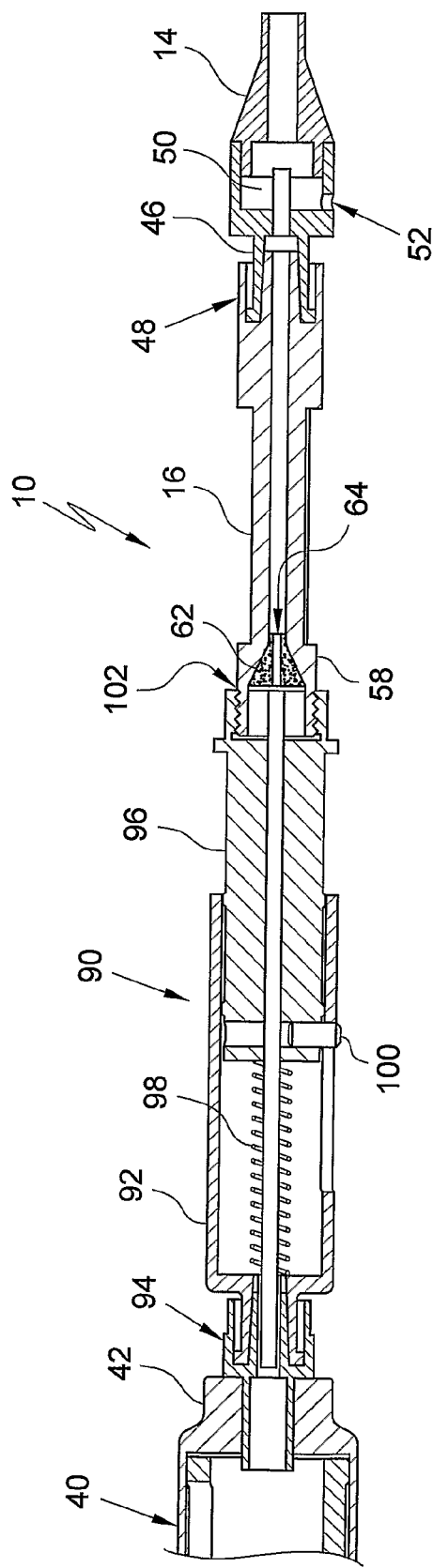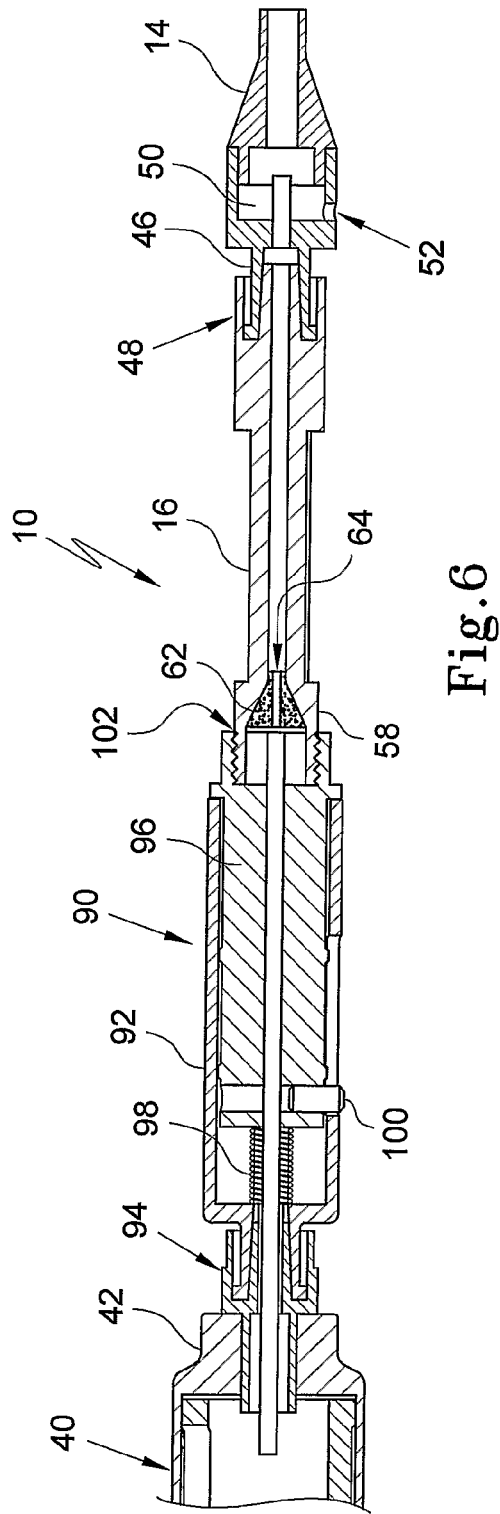

IRRIGATION CATHETER

CROSS-REFERENCE TO RELATED APPLICATIONS

This application is a National Phase filing under 35 U.S.C. §371 of International Application No. PCT/AU2006/001791, filed Nov. 27, 2006, which claims the benefit of U.S. Provisional Patent Application No. 60/753,836, filed on Dec. 23, 2005, the contents of which are incorporated herein by reference in their entirety.

TECHNICAL FIELD

This invention relates, generally, to catheters and, more particularly, to an irrigation catheter assembly and to a catheter including such assembly.

BACKGROUND

In the heat treatment of a biological site in a patient's body, it is often necessary to cool the site being treated. This is effected by an appropriately sterilized liquid being applied at the site.

The Applicant has filed an International Patent Application for an electrical lead under International Patent Application Number PCT/AU01/01339 dated Oct. 19, 2001. The electrical lead forming the subject matter of the International Patent Application has an unimpeded lumen and is suitable as an electrode sheath of an irrigation catheter. It lends itself to this application due to the fact that the unimpeded lumen facilitates insertion of items to assist in maneuvering and manipulating the electrode sheath while retaining a narrow diameter sheath, which is beneficial in steering the catheter through the vascular system of the patient to the site of interest. The lumen can also be used as a conduit for the passage of the irrigation fluid to the distal end of the catheter to be emitted at the distal end.

Throughout this specification, the word "comprise," or variations such as "comprises" or "comprising," will be understood to imply the inclusion of a stated element, integer or step, or group of elements, integers or steps, but not the exclusion of any other element, integer or step, or group of elements, integers or steps.

DISCLOSURE

According to a first aspect of the invention, there is provided an irrigation catheter assembly that comprises:
  an electrode sheath mount for mounting an electrode sheath, the mount having a laterally arranged aperture defined in it through which conductors for electrodes of the electrode sheath pass, in use; and
  a connector, to which a source of irrigation fluid is connectable, connected to a proximal end of the electrode sheath mount, the connector communicating with an interior of the mount so that, in use, fluid passes through the lumen of the electrode sheath to be delivered to a distal end of the electrode sheath.

The assembly may include a handle, a proximal end of the connector being connectable to the handle. The handle may be free of electrical connectors. In other words, there is an absence of electrical connectors and electrical conductors within the handle. The conductors for electrodes of the electrode sheath may be in a bundle passing through the aperture and may terminate in a cable connector at a proximal end of the conductor bundle. The conductor bundle and the cable connector may be arranged externally of the handle and may adopt a coiled telephone cord configuration for ease of use. One end of a patient cable may be connected directly to the cable connector with an opposed end of the patient cable being connected to a power or radio frequency (RE) source.

The assembly may include a pressure feedback unit mounted on the handle.

The connector may be carried on a distal end of the pressure feedback unit.

Preferably, the connector is a Y-connector. A proximal end of the connector may carry a seating element, which seals against an elongate element receivable in a lumen of the electrode sheath, in use, the sealing element inhibiting the ingress of material into the handle.

According to a second aspect of the invention, there is provided an irrigation catheter assembly that comprises:
  a handle to which an elongate element is attachable;
  an electrode sheath mount, for mounting an electrode sheath, attached to the handle, so that, in use, the elongate element is received in a lumen of the electrode sheath;
  a connector, to which a source of irrigation fluid is connectable, associated with the handle, the connector communicating with an interior of the mount so that, in use, fluid passes through the lumen, containing the elongate element, of the electrode sheath to be delivered to a distal end of the electrode sheath; and
  a sealing element that is deformable, in use, into sealing engagement with the elongate element by attachment of the connector to the handle to inhibit ingress of material into the handle.

The assembly may include the elongate element and the elongate element may be a steering device that is used to steer a distal portion of the electrode sheath, the handle including a catheter steering control mechanism for controlling the steering device.

Once again, the handle may be free of electrical connectors.

The assembly may include a pressure feedback unit mounted on the handle.

The connector may be carried on a distal end of the pressure feedback unit.

Preferably, the connector is a Y-connector.

According to a third aspect of the invention, there is provided an irrigation catheter handle assembly that comprises:
  an elongate body, the body being free of electrical connectors; and
  a mounting arrangement carried by the body for mounting an elongate element receivable in a lumen of an electrode sheath connectable to the elongate body.

A catheter steering control mechanism may be carried on the body, the steering control mechanism, in use, cooperating with the elongate element, mounted to the body in use, for steering a distal portion of the electrode sheath.

The assembly may include a connector, to which a source of irrigation fluid is connectable, arranged distally of the body.

The assembly may include an electrode sheath mount attached to a distal end of the connector, for mounting an electrode sheath. The electrode sheath mount may have a lateral aperture defined in it through which conductors of the electrode sheath pass, in use.

A displacement mechanism may be carried on the body, the displacement mechanism facilitating relative longitudinal displacement between the steering device and the electrode sheath, in use.

The invention extends also to an irrigation catheter that includes:

an assembly as described above; and an electrode sheath attached to the electrode sheath mount.

A distal end of the catheter may have at least one aperture through which the irrigation fluid is discharged from the electrode sheath. The at least one aperture may be defined in an electrode carried on the distal end of the electrode sheath.

Instead, the electrode sheath may carry a return line in it via which irrigation fluid is returned from a distal end to a proximal end of the electrode sheath.

At least one of a steering device, a deflectable curve stylet, a fixed curve stylet and a complex shape stylet may be received in a lumen of the electrode sheath.

BRIEF DESCRIPTION OF THE DRAWINGS

FIG. 5 shows a sectional side view of a part of an irrigation catheter handle assembly, in accordance with a second embodiment of the invention, in a first condition; and FIG. 6 shows a sectional side view of the part of the handle assembly of FIG. 5 in a second condition.

DETAILED DESCRIPTION OF THE INVENTION

Figure 1:
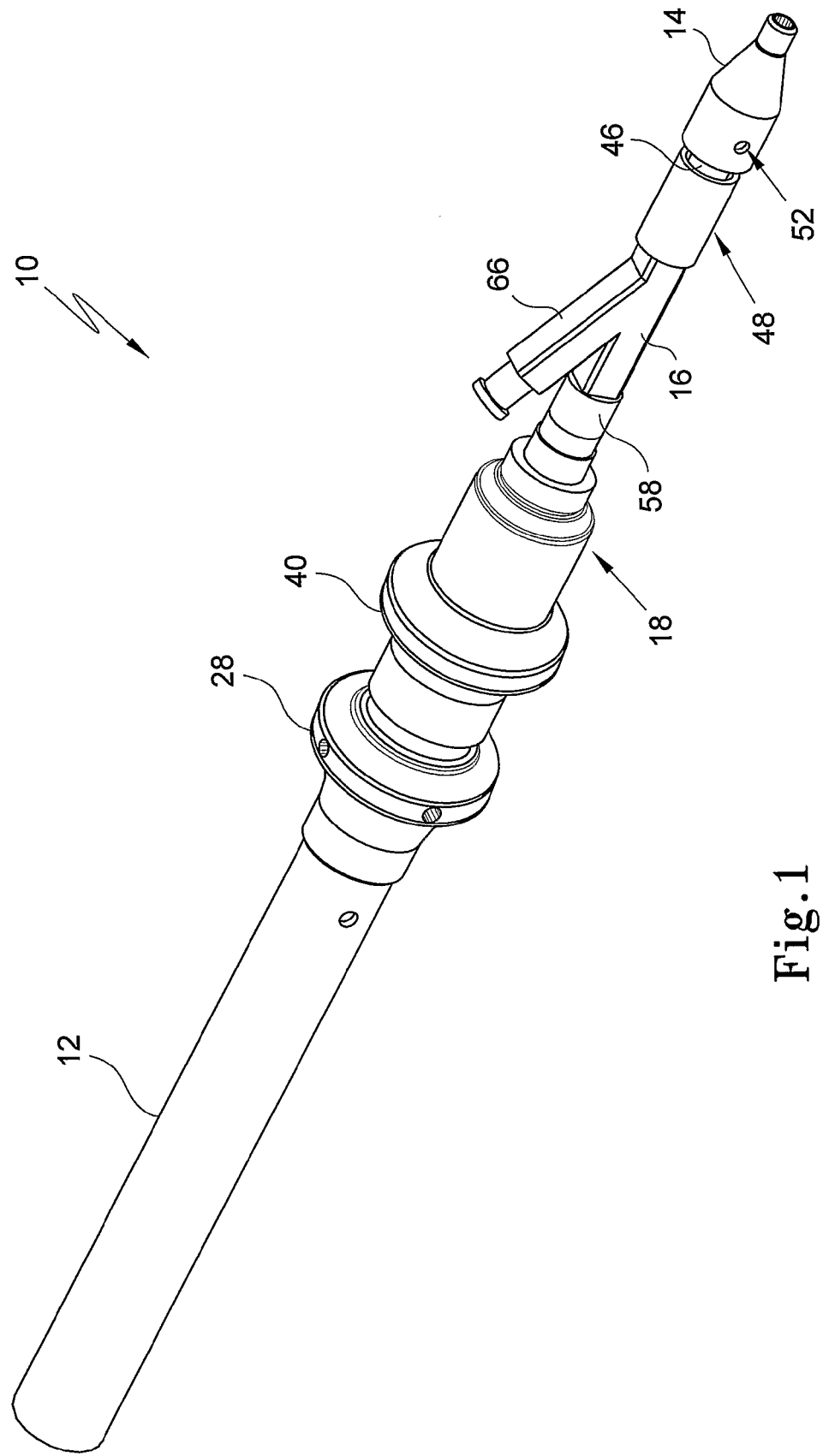
FIG. 1 shows a three-dimensional view of an irrigation catheter handle assembly, in accordance with a first embodiment of the invention.
Figure 2:
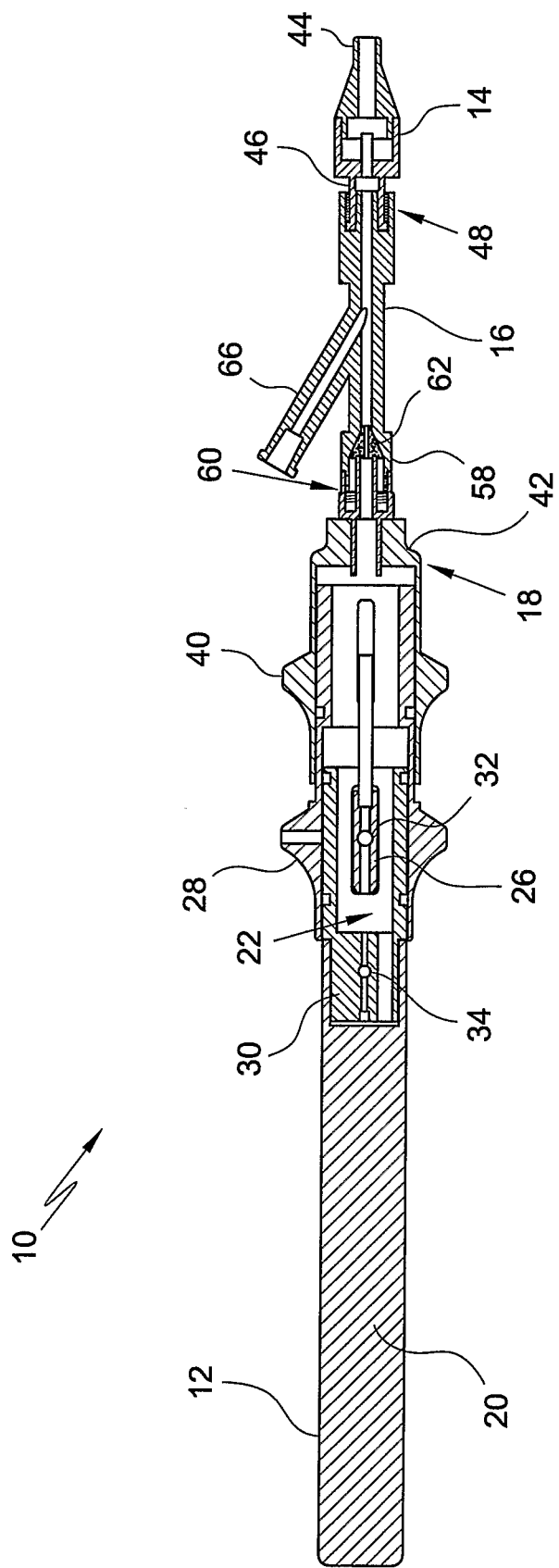
FIG. 2 shows a sectional side view of the handle assembly of FIG. 1.

Referring initially to FIGS. 1 and 2 of the drawings, an irrigation catheter handle assembly, in accordance with a first embodiment of the invention, is shown, and is designated generally by the reference numeral 10. The assembly 10 comprises a handle 12, an electrode sheath mount 14 and a connector 16 via which the mount 14 is mounted to a distal end 18 of the handle 12. Referring to FIG. 2 of the drawings, it is to be noted that the handle 12 has a solid central portion 20 and is free of electrical connectors and, optionally, electrical conductors.

A bore 22 at a distal end of the handle 12 receives a proximal end of a steering device or steering shaft. The steering shaft is not shown in FIGS. 1 and 2 of the drawings but is illustrated schematically at 24 in FIG. 4 of the drawings.

The steering shaft 24 used with the catheter handle is of the type described in the Applicant's International Application No. PCT/AU2005/000216 dated Feb. 18, 2005, entitled "A steerable catheter." Thus, the steering shaft 24 includes a tubular member in which an actuator is slidably received. The tubular member has a cutaway portion at a distal region, which forms a bend-enhancing zone. A distal part of the actuator is fast with a distal part of the tubular member distally of the bend-enhancing region. Relative longitudinal movement of the tubular member and the actuator relative to each other causes bending of the tubular member and, hence, the electrode sheath of the catheter in which the steering shaft 24 is mounted.

The handle 12 of the assembly 10 includes a first anchoring formation 26 formed integrally with a steering control mechanism in the form of a slide 28. A second anchoring formation 30 is formed integrally with the handle 12. The slide 28 is longitudinally displaceable relative to the handle 12. The tubular member of the steering shaft 24 is connectable to one of the anchoring formations 26 or 30 with the actuator of the steering shaft 24 being connectable to the other anchoring formation 26 or 30. To facilitate modularity of the assembly 10, the components of the steering shaft 24 are releasably connectable to the anchoring formations 26, 30. Thus, the components of the steering shaft 24 securable to the slide 28 and handle 12, respectively, are secured in position relative to the anchoring formations 26, 30 via grub screws (not shown) received in threaded openings 32, 34, respectively.

When the slide 28 is displaced relative to the handle 12, relative longitudinal movement between the components of the steering shaft 24 occurs and steering of a distal end of an electrode sheath 36 (FIG. 3) of a catheter 38 occurs, the electrode sheath 36 being mounted on the mount 14.

Further, to improve flexibility of a distal end of the electrode sheath 36, the steering shaft 24 and the electrode sheath 36 are longitudinally displaceable relative to each other so that a distal end of the electrode sheath 36 can be moved out of register with the distal end of the steering shaft 24. This is facilitated by a second slide 40 arranged distally of the slide 28 on the handle body 12 and slidable relative to the slide 28 and the handle body 12.

A distal end 42 of the slide 40 supports the connector 16 and, in turn, the electrode sheath mount 14.

A proximal end of the electrode sheath 36 is mounted on a distal portion 44 of the electrode sheath mount 14. A proximal end 46 of the electrode sheath mount 14 is mounted to a distal end of the connector 16 via a Luer-lock type arrangement.

A lateral aperture 52, communicating with an interior 50 of the mount 14, is defined in a side wall of the mount 14. The aperture 52 is shown most clearly in FIGS. 5 and 6 of the drawings.

Figure 3:
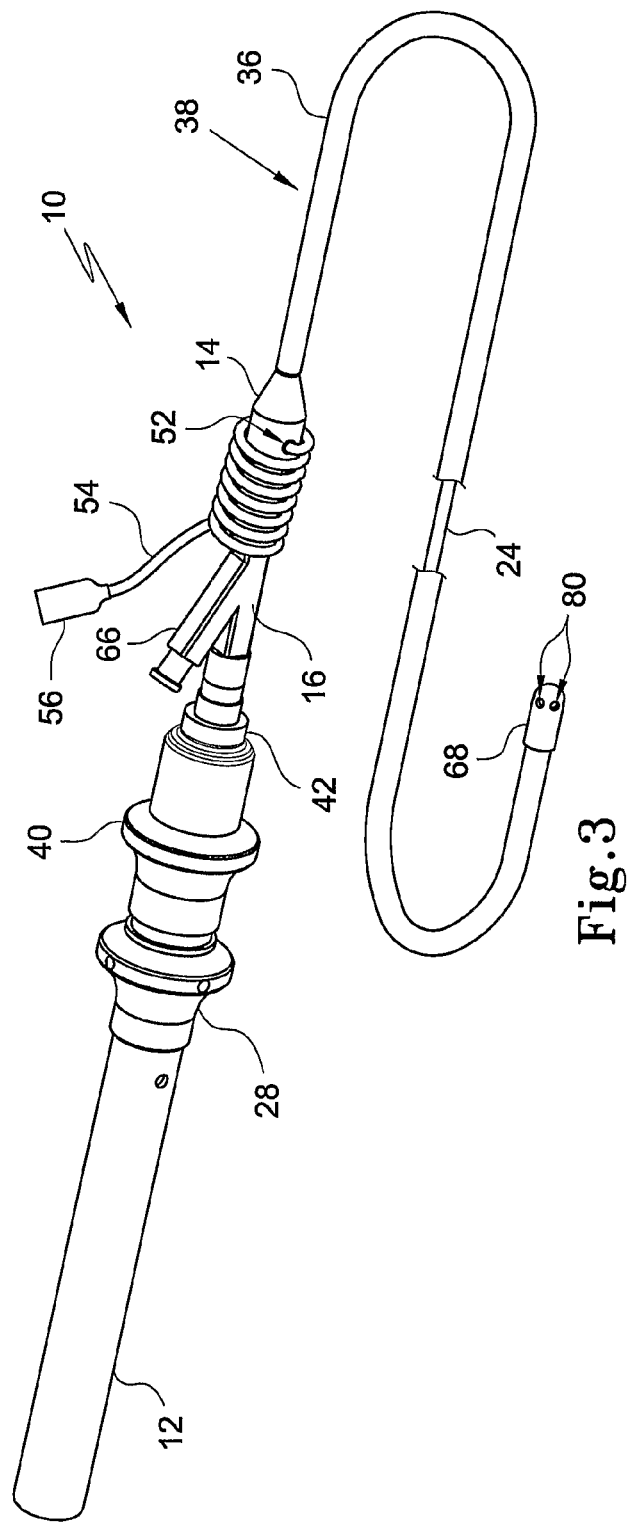
FIG. 3 shows a three dimensional, schematic view of a catheter including the handle assembly of FIGS. 1 and 2.

As illustrated in FIG. 3 of the drawings, a bundle of electrical conductors 54 for electrodes of the electrode sheath 36 pass out of the aperture 52. The bundle of conductors 54 are arranged in a coiled, telephone cord-like manner around the connector 16 before diverging laterally as shown in FIG. 3 of the drawings. The bundle of electrical conductors 54 terminates in a connector 56 to which a patient cable (not shown) is directly connected. Therefore, with this arrangement, the handle 12 does not need to have connectors or electrical conductors. This reduces the costs of the handle 12 and also facilitates its modularity to enable it to be reused.

The connector 16 is a Y-connector having the sheath mount 14 arranged on its distal end. A proximal end 58 of the connector 16 is connected via a screw thread arrangement 60 to the distal end 42 of the slide 40. A sealing element 62 in the form of a frusto-conical, elastomeric member is arranged inwardly of the proximal end 58 of the connector 16.

The sealing element 62 has a passage 64 (FIGS. 5 and 6) extending through it through which the steering shaft 24 passes. When the proximal end 58 of the connector 16 is mounted on the distal end 42 of the slide 40, the sealing element 62 is deformed radially inwardly urging the sealing element 62 into sealing engagement with the steering shaft 24. This inhibits the back flow of liquids, in particular, irrigation solution into the distal end of the handle 12.

The Y-connector 16 has a lateral element 66 to which a source of irrigation fluid (not shown), such as saline solution, is connected to irrigate a biological site in a patient's body being treated by the catheter 38.

Figure 4:
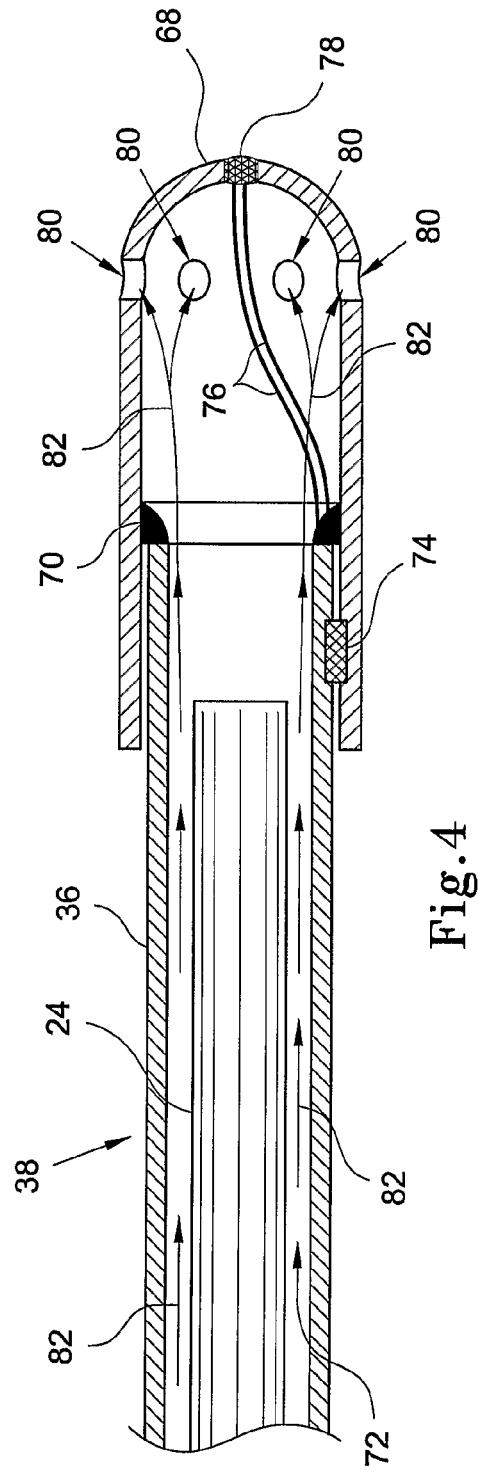
FIG. 4 shows a sectional side view of a distal end of the catheter of FIG. 3.

Referring to FIGS. 3 and 4 of the drawings, an ablating electrode 68 is arranged at a distal end of the electrode sheath 36 of the catheter 38. The ablating electrode 68 is mounted on a distal end of the electrode sheath 36. The distal end of the electrode sheath 36 is sealed by an epoxy 70 (FIG. 4) to inhibit the ingress of moisture into the interior of the electrode sheath 36. The electrode sheath 36 is, as described above, manufactured in accordance with the Applicant's International Patent Application No. PCT/AU01/01339, referenced above. Thus, a lumen 72 of the electrode sheath 36 is unimpeded by electrical conductors, the electrical conductors being embedded within the wall of the electrode sheath 36.

An electrical connection is formed between the electrode 68 and an appropriate conductor within the electrode sheath 36 via an electrical connection 74. Similarly, electrical conductors 76 protrude through the epoxy 70 and connect to a temperature sensor 78 arranged at an end of the electrode 68.

The electrode 68 has a plurality of circumferentially spaced openings 80 formed therein. The saline solution is expelled or ejected through these openings 80 to irrigate a biological site being treated by the electrode 68. More particularly, the saline solution inhibits charring and thrombosis formation at the site. It is to be noted that the saline solution passes about the steering shaft as indicated by arrows 82. Instead of the openings, the irrigation solution could flow through the interior of the electrode 68 to cool the electrode 68. The irrigation solution could then be drawn up through a conduit in the wall of the electrode sheath 36 for cooling and re-use.

Referring now to FIGS. 5 and 6 of the drawings, a second embodiment of a catheter handle assembly is illustrated. With reference to FIGS. 1 to 4 of the drawings, like reference numerals refer to like parts, unless otherwise specified.

In this embodiment, a pressure feedback unit 90 is interposed between the distal end 42 of the slide 40 and the connector 16.

The pressure feedback unit 90 is used for monitoring the pressure applied by the ablation electrode 68 at the site being treated and to inhibit perforation of a patient's organs or vascular system.

The pressure feedback unit 90 comprises a cylinder 92. A proximal end of the cylinder 92 is connected to the distal end 42 of the slide 40 via a Luer-lock arrangement 94. A piston 96 is slidably disposed within the cylinder 92 to project out of a distal end of the cylinder 92. The piston 96 is urged to the position shown in FIG. 5 of the drawings by an urging device in the form of a coil spring 98.

Thus, the arrangement shown in FIG. 5 of the drawings is with the piston 96 extended relative to the cylinder 92, i.e., the rest condition of the piston 96. The arrangement shown in FIG. 6 of the drawings is with the piston 96 urged into the interior of the cylinder 92 against the action of the coil spring 98, i.e., when pressure is being exerted on the electrode sheath 36 of the catheter 38.

An indicator 100 is provided on the pressure feedback unit 90 so that a clinician can readily determine the pressure being exerted by the ablation electrode 68.

In this embodiment, instead of a Luer-lock arrangement 60 at the proximal end 58 of the connector 16, the proximal end 58 of the connector 16 is screw threadedly received in the piston 96 as shown at 102 in the drawings. Once again, when the proximal end 58 of the connector 16 is received in the piston 96, the sealing element 62 is deformed radially inwardly urging the sealing element 62 into sealing engagement with the steering shaft 24.

It is an advantage of the invention that an irrigation catheter is provided that has components that are able to be re-used. In particular, the handle and the steering shaft can be reused after appropriate cleaning and sterilization. The use of the sealing element inhibits ingress of fluids into the handle.

It is yet a further advantage of the invention that a catheter handle is provided that has an absence of electrical connectors and electrical cables. This considerably reduces the cost of the handle. It also renders it more suitable for re-use.

The modularity of the assembly is improved by the Luer-lock connections of the components to one another. Thus, if desired, the Y-connector can be removed if no irrigation is needed.

Finally, the use of the pressure feedback unit allows a clinician to determine the pressure being exerted by the ablation electrode, thereby reducing the risk of perforations.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An irrigation catheter assembly comprising:
an electrode sheath mount mounting a proximal end of an electrode sheath to a distal portion of the electrode sheath mount, the electrode sheath extending over a terminal edge of the electrode sheath mount, the electrode sheath being flexible, the electrode sheath mount having a laterally arranged aperture defined in it through which conductors for electrodes of the electrode sheath pass, in use;
a connector, to which a source of irrigation fluid is connectable, the connector being releasably connected at its distal end to a proximal end of the electrode sheath mount, the connector communicating with an interior of the electrode sheath mount so that, in use, fluid passes through the lumen of the electrode sheath to be delivered to a distal end of the electrode sheath; and
a handle connectable to a proximal end of the connector, wherein the handle is free of electrical connectors and electrical conductors.

2. The irrigation catheter assembly of claim 1, further comprising a pressure feedback unit mounted on the handle, the pressure feedback unit configured to monitor the pressure applied by the distal end of the electrode sheath to a part of the body of a patient.

3. The irrigation catheter assembly of claim 2, wherein the connector is carried on a distal end of the pressure feedback unit.

4. The irrigation catheter assembly of claim 1, wherein the connector is a Y-connector.

5. The irrigation catheter assembly of claim 1, wherein a proximal end of the connector carries a sealing element that seals against an elongate element receivable in a lumen of the electrode sheath, in use, the sealing element inhibiting the ingress of material into the handle.

6. An irrigation catheter assembly, comprising:
a handle to which an elongate element is attached;
an electrode sheath mount mounting a proximal end of an electrode sheath to a distal portion of the electrode sheath mount, the electrode sheath being flexible, the electrode sheath mount attached to the handle, so that, in use, the elongate element is a steering device received in a lumen of the electrode sheath and is configured to steer a distal portion of the electrode sheath;
a connector, to which a source of irrigation fluid is connectable, associated with the handle, the connector being releasably connected at its distal end to a proximal end of the electrode sheath mount, and the connector communicating with an interior of the electrode sheath mount so that, in use, fluid passes through the lumen, containing the elongate element, of the electrode sheath to be delivered to a distal end of the electrode sheath; and
a sealing element that is deformable, in use, into sealing engagement with the elongate element by attachment of the connector to the handle to inhibit ingress of material into the handle.

7. The irrigation catheter assembly of claim 6, the handle including a catheter steering control mechanism for controlling the steering device.

8. The irrigation catheter assembly of claim 6, wherein the handle is free of electrical connectors.

9. The irrigation catheter assembly of claim 6, further comprising a pressure feedback unit mounted on the handle.

10. The irrigation catheter assembly of claim 9, wherein the connector is carried on a distal end of the pressure feedback unit.

11. The irrigation catheter assembly of claim 6, wherein the connector is a Y-connector.

12. An irrigation catheter handle assembly, comprising:
an elongate body, the elongate body being free of electrical connectors and electrical conductors;
at least one anchoring formation carried by the elongate body and anchoring an elongate element received in a lumen of an electrode sheath, a proximal end of the electrode sheath mounted to a distal portion of an electrode sheath mount, the electrode sheath extending over a terminal edge of the electrode sheath mount, and the electrode sheath mount being releasably connectable to the elongate body; and
a connector to which a source of irrigation fluid is connectable, the connector communicating with an interior of the electrode sheath mount so that, in use, fluid passes through the lumen of the electrode sheath to be delivered to a distal end of the electrode sheath.

13. The irrigation catheter handle assembly of claim 12, further comprising a catheter steering control mechanism carried on the elongate body, the steering control mechanism, in use, cooperating with the elongate element, the steering control mechanism mounted to the elongate body, in use, for steering a distal portion of the electrode sheath.

14. The irrigation catheter handle assembly of claim 12, wherein the electrode sheath mount is, in use, releasably connected at its proximal end to a distal end of the connector.

15. The irrigation catheter handle assembly of claim 14, wherein the electrode sheath mount has a lateral aperture defined in it through which conductors of the electrode sheath pass, in use.

16. The irrigation catheter handle assembly of claim 14 further comprising a displacement mechanism carried on the elongate body, the displacement mechanism facilitating relative longitudinal displacement between the elongate element and the electrode sheath, in use.

17. An irrigation catheter, comprising:
an assembly, comprising:
a handle having an elongate body, the elongate body being free of electrical connectors and electrical conductors;
an anchoring formation carried by the elongate body anchoring an elongate element received in a lumen of an electrode sheath, the electrode sheath being flexible, a proximal end of the electrode sheath mounted to a distal portion of an electrode sheath mount, the electrode sheath extending over a terminal edge of the electrode sheath mount, the electrode sheath mount being releasably connectable to the elongate body; and
a connector, to which a source of irrigation fluid is connectable, arranged distally of the elongate body, wherein the electrode sheath mount is, in use, releasably connected at its proximal end to a distal end of the connector, for mounting the electrode sheath.

18. The irrigation catheter of claim 17, wherein a distal end of the electrode sheath has at least one aperture through which the irrigation fluid is discharged from the electrode sheath.

19. The irrigation catheter of claim 18, wherein the at least one aperture is defined in an electrode carried on the distal end of the electrode sheath.

20. The irrigation catheter of claim 17, wherein the electrode sheath carries a return line in it via which irrigation fluid is returned from a distal end to a proximal end of the electrode sheath.

21. The irrigation catheter of claim 17, wherein at least one of a steering device, a deflectable curve stylet, a fixed curve stylet and a complex shape stylet is received in a lumen of the electrode sheath.

22. The assembly of claim 1, wherein the connector is releasably connectable at its proximal end to the handle, the handle including a steering control mechanism, the steering control mechanism supporting a steering device that, in use, extends inside the lumen of the electrode sheath thereby to enable steering of the distal portion of the electrode sheath.

23. The assembly of claim 6, wherein the connector is releasably connectable at its proximal end to the handle, the handle including a steering control mechanism, the steering control mechanism supporting the elongate element.

24. The assembly of claim 12, wherein the connector is releasably connectable at its proximal end to the elongate body, the elongate body carrying a steering control mechanism, the steering control mechanism supporting the elongate element, the elongate element, in use, extending inside the lumen of the electrode sheath thereby to enable steering of a distal portion of the electrode sheath.

* * * * *